(12) United States Patent
Grim (10) Patent No.: US 7,513,899 B2
(45) Date of Patent: Apr. 7, 2009

(54) ACETABULAR REAMER CONNECTION MECHANISM

(75) Inventor: Gregory Andrew Grim, Morris Plains, NJ (US)

(73) Assignee: Howmedica Osteonics Corp., Mahwah, NJ (US)

(*) Notice: Subject to any disclaimer, the term of this patent is extended or adjusted under 35 U.S.C. 154(b) by 224 days.

(21) Appl. No.: 11/342,206

(22) Filed: Jan. 27, 2006

(65) Prior Publication Data

US 2007/0191854 A1    Aug. 16, 2007

(51) Int. Cl.
*A61B 17/00* (2006.01)
(52) U.S. Cl. .................. 606/80; 606/79; 606/81
(58) Field of Classification Search ............ 606/1, 606/79, 80, 84, 81; 279/79; 403/325, 326, 403/399; 81/177.85
See application file for complete search history.

(56) References Cited

U.S. PATENT DOCUMENTS

| | | | |
|---|---|---|---|
| 3,702,611 A | 11/1972 | Fishbein | |
| 4,305,394 A | 12/1981 | Bertuch, Jr. | |
| 4,632,111 A | 12/1986 | Roche | |
| 5,037,424 A | 8/1991 | Aboczsky | |
| 5,061,270 A | 10/1991 | Aboczky | |
| 5,320,625 A | 6/1994 | Bertin | |
| 5,501,686 A | 3/1996 | Salyer | |
| 5,658,290 A | 8/1997 | Lechot | |
| 6,283,972 B1 | 9/2001 | Riley | |
| 6,395,005 B1 | 5/2002 | Lovell | |
| 6,782,581 B2 * | 8/2004 | Block ............... | 15/250.32 |
| 6,854,742 B2 | 2/2005 | Salyer et al. | |
| 2002/0099380 A1 * | 7/2002 | Salyer et al. ............ | 606/80 |
| 2003/0216716 A1 * | 11/2003 | Desarzens ............ | 606/1 |
| 2004/0116935 A1 | 6/2004 | Lechot | |
| 2005/0124981 A1 | 6/2005 | Desarzens et al. | |

* cited by examiner

*Primary Examiner*—Eduardo C Robert
*Assistant Examiner*—Andrew Yang
(74) *Attorney, Agent, or Firm*—Lerner, David, Littenberg, Krumholz & Mentlik, LLP (57) ABSTRACT

A tool holder releasably coupling a surgical tool such as a reaming tool to a drive shaft which tool has radially extending mounting elements. The holder includes a head portion coupled to an end of the drive shaft, the head portion having a body with an outwardly open groove extending thereacross for receiving the radially extending mounting elements on the tool. The mounting elements may be in the form of rods adapted to be received within the groove which rods extend across a base of the tool. The head portion includes a bore extending through the body in communication with the groove. A biased lock pin is slidably mounted in the bore of the head portion and is biased into a position whereby the locked pin engages the rod and locks it in place. A spring-biased lock collar is provided having stop surfaces thereon for engaging two stop surfaces on the lock pin a first locking the lock pin in the locked position and a second maintaining the lock pin in the open position.

23 Claims, 11 Drawing Sheets

ACETABULAR REAMER CONNECTION MECHANISM

BACKGROUND OF THE INVENTION

The present invention is directed to implantation of artificial joint components and in particular to acetabular joint components. More particularly, it relates to an instrument for reaming the acetabular socket which allows the connection of and removal of an acetabular reamer. While the instrument is described in connection to an acetabular reamer, it should be noted that the connection mechanism disclosed can be used with any tool. In the case of a reamer, there is a drive shaft located within the tool for rotating the instrument.

Total hip replacement or arthroplasty operations have been performed to repair the acetabulum and the region surrounding it and to replace the hip components such as the natural femoral head and acetabular socket which have degenerated.

With regard to the acetabulum, many instruments have been designed to locate either the acetabular cup or provide reamers for repairing the acetabulum to receive such a prosthetic cup. Such instruments are shown in U.S. Pat. Nos. 4,305,394, 4,632,111, 5,037,424, 5,061,270, 5,320,625, and 6,395,005.

In addition, there have been various designs for the acetabular reamers themselves, including the reamer and holder shown in U.S. Pat. No. 5,658,290. A similar reamer is shown in U.S. Publication No. 2005/0124981 along with a holder for the same. While these patents show holders for mounting the reamer via a drive shaft to a power source, it has been found that an improved connect and removal disconnect mechanism would be desirable.

In general, such instruments include a shank or handle portion which is hollow and houses a rotatable drive holder. The head includes the quick disconnect for coupling, for example, an acetabular reamer having a hemispherical cutting surface and preferably four rods, bars, or other coupling elements extending from a central hub area preferably located adjacent the equator of the hemispherical cutting surface. Of course the hub could be eliminated with the bars extending continuously across the reamer and the rods or bars could be recessed within the reamer cavity.

Generally orthopedic reaming, including acetabular reaming, utilizes a series of reamers which increase in size in one or two millimeter steps. These reamers are used in series to enlarge an opening for the receipt of a prosthetic implantation. Incremental reamers are required because excessive heat is generated if the surgeon tries to remove too much tissue or bone with a single reamer. In addition, surgeons may wish to remove the reamer either in the wound or outside thereof to verify the size, bone condition, and implant orientation. Because of this the surgeon must be able to connect and disconnect the reaming tool from the holder preferably in a simple, easy step, and replace a first reamer with a second reamer positively and quickly.

SUMMARY OF THE INVENTION

It is one aspect of the present invention to provide a tool holder which may be used for quickly connecting a series of tools preferably to a rotary drive system which includes a power source and a drive shaft.

It is yet another aspect of the invention to provide a surgical tool holder which can couple a series of reaming instruments to a rotary drive shaft.

These aspects are provided by a tool holder for selectively rotatably coupling a tool having mounting elements such as rods or bars extending across an end of the tool preferably radially extending mounting elements to a drive shaft. The tool holder includes a head portion coupled to an end of the drive shaft. The head portion has a body with an outwardly open groove or grooves extending across one face thereof for receiving the preferably radially extending rod on the tool. The head also includes one or more bores extending through the body in communication with the grooves. Preferably the bores extend in a direction perpendicular to the long axis of the grooves to which they communicate. A spring biased lock pin is slidably mounted in each bore of the head portion. Preferably the spring is a coil spring however any elastic element which can bias the lock pin within the bore can be utilized. The lock pin has a recess therein for receiving the mounting element or rod with the elastic element biasing the lock pin into a first position wherein the lock pin recess is aligned with the groove in the head portion. The lock pin recess has a cam surface engagable with the mounting elements thereon and two stop surfaces extending beyond a periphery of the head portion when the lock pin is in the first position. Upon insertion of the mounting elements or rods into the recess on the lock pin, the cam surface is engaged and moves the lock pin against the elastic elements or spring into a second position engaging the second stop surface wherein at least part of the recess is not aligned with the groove to thereby lock the mounting element or rod within the head.

A spring biased lock collar is slidably mounted on the head with the lock collar having a stop surface thereon for engaging the stop surfaces on the lock pin(s). The lock collar is spring biased into a position wherein the stop surface thereon engages the stop surface on the lock pin and wherein the first stop surface on the lock pin and the lock collar disengage and the second stop surface engages when the lock pin is moved to the second position. This allows the spring to move the lock collar with respect to the head to a second position which prevents the lock pin from moving to the first position.

Preferably the head portion has two grooves each having a lock pin bore associated therewith and each bore having a spring biased lock pin slidably mounted therein. Preferably the two lock pin bores are parallel to one another and the two grooves are perpendicular to one another. However, three or even four lock pins and bores are possible. In the preferred embodiment, the grooves are adapted to receive mutually perpendicular mounting elements or rods on the tool. Thus the two lock pins engage a single rod of the mutually perpendicular rods. If the two lock pin bores are perpendicular to one another then a single lock pin will engage each of the mutually perpendicular rods. Preferably the four radially extending mounting elements or rods on the tool extend outwardly from a central hub portion with at least two of the rods engaging in each of the two grooves. The four rods extend outwardly at 90 degrees increments around the hub. The lock collar includes recesses for receiving the rod when it is in its extended position.

When used as a reamer or rotary cutting tool holder, both the lock collar and the head portion are rotatably mounted on a drive shaft within the handle, and thus can rotate with respect to the handle.

Each lock pin recess has a first open portion for receiving the mounting elements and a part cylindrical portion for seating the mounting elements. A center of the part cylindrical seating portion being offset from the center of the recessed open portion in a direction of the tool longitudinal axis of the lock pin bore in the body portion of the head portion. A wall extending between the first and second lock pin recessed portions forms the cam surface which engages the rods on insertion of the tool into the grooves of the head portion. This engagement moves the lock pin into the second position. A line connecting the centers of the first and second recessed portions extends at an angle with respect to the longitudinal axis of the lock pin bore preferably at 45 degrees.

DETAILED DESCRIPTION

Figure 1:
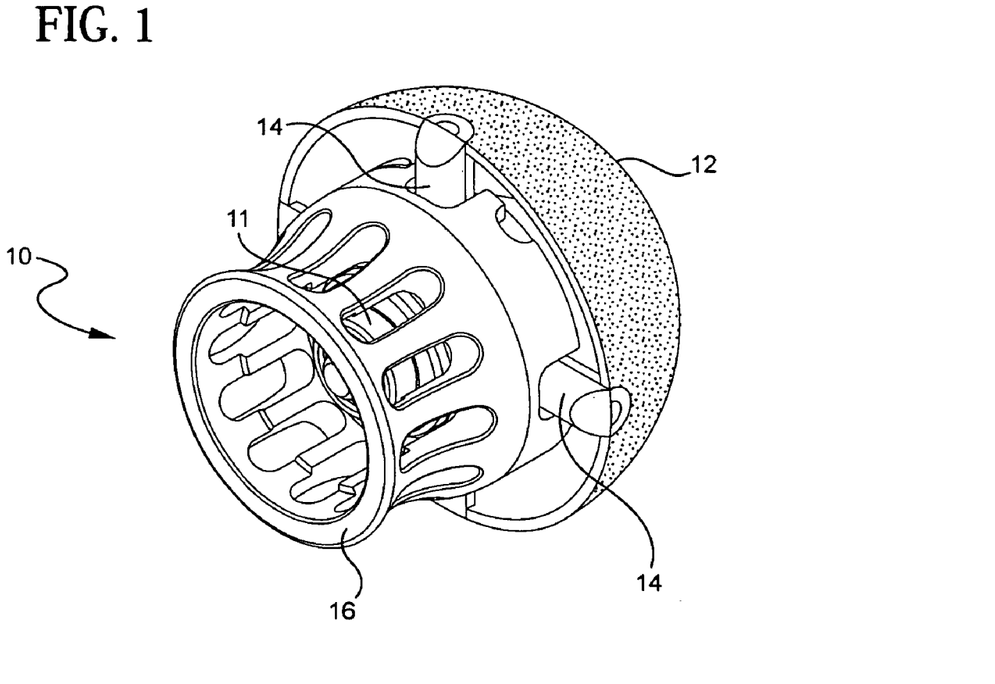
FIG. 1 is a bottom isometric view of the tool holder of the present invention.
Figure 2:
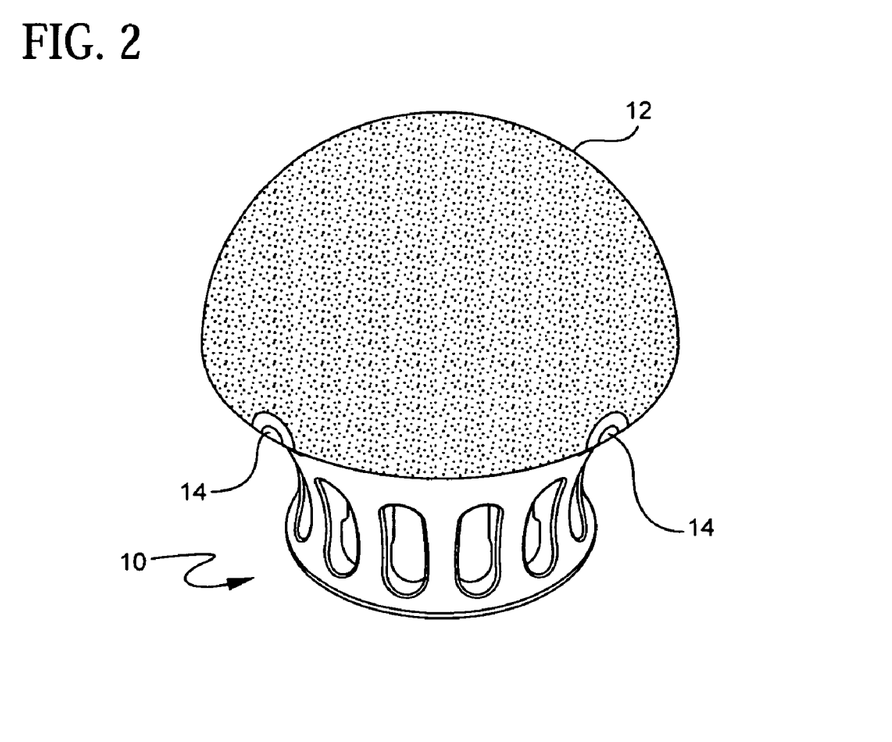
FIG. 2 is a top perspective view of the tool holder shown in FIG. 1.

Referring to FIG. 1 there is shown a perspective view of the tool holder assembly of the present invention generally denoted as 10. The assembly includes a lock collar 16 slidably mounted on a tool mounting head 11. The tool holder assembly is shown having a hemispherical acetabular reamer 12 mounted thereon. The mounting is via the engagement of tool mounting head 11 on one or more mounting elements such as rods 14 which are integral with reamer 12. FIG. 2 shows the assembly of FIG. 1 looking down from the top.

Figure 3:
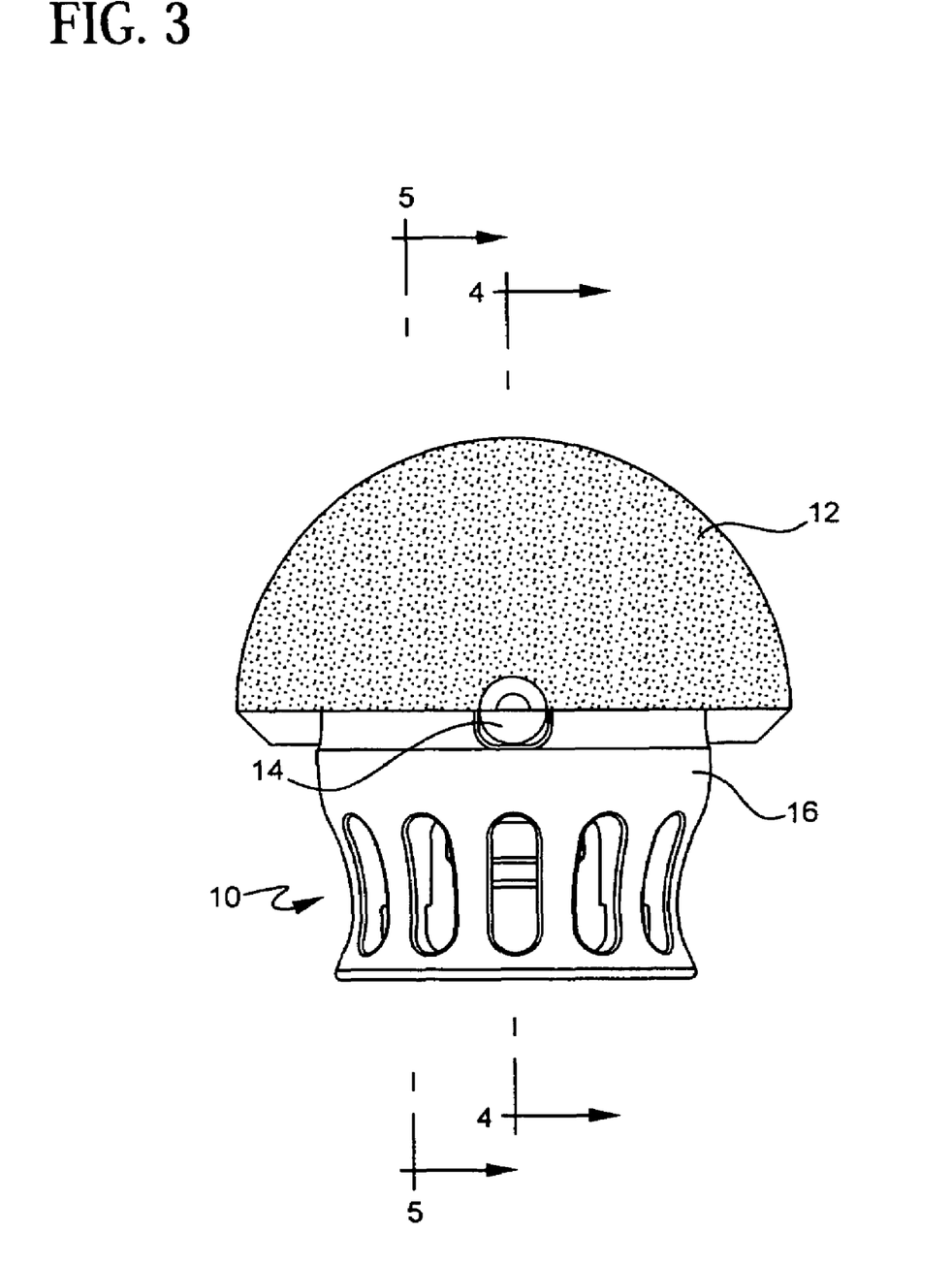
FIG. 3 is an elevation view of the tool holder of FIGS. 1 and 2.

Referring to FIG. 3 there is shown a side elevation view of the assembly of FIG. 1 in which the lock collar 16 of tool mounting head 11 is clearly shown. As can be seen in FIGS. 1 through 3, mounting elements or rods 14 of the preferred tool, which is an acetabular reamer, extend across reamer 12 and are, in the preferred embodiment, mutually perpendicular. In the preferred embodiment, rods 14 are cylindrical. However, they could have other cross-sectional shapes or even be in the form of half cylindrical cross elements. It should be noted that while an acetabular reamer 12 is shown, any tool or implant having at least one, and preferably two, three or four mounting elements can be engaged by the tool mounting holder or head 10.

Figure 4:
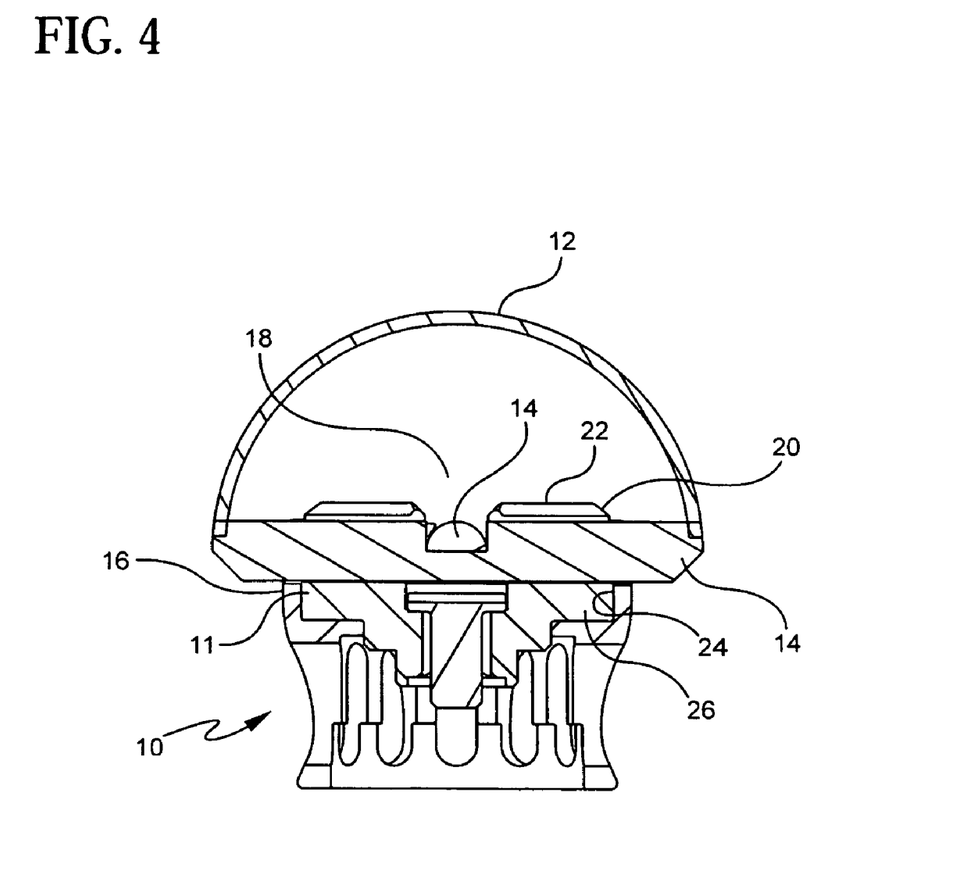
FIG. 4 is a cross-sectional view of the tool holder of FIG. 3 along lines 4-4.
Figure 5:
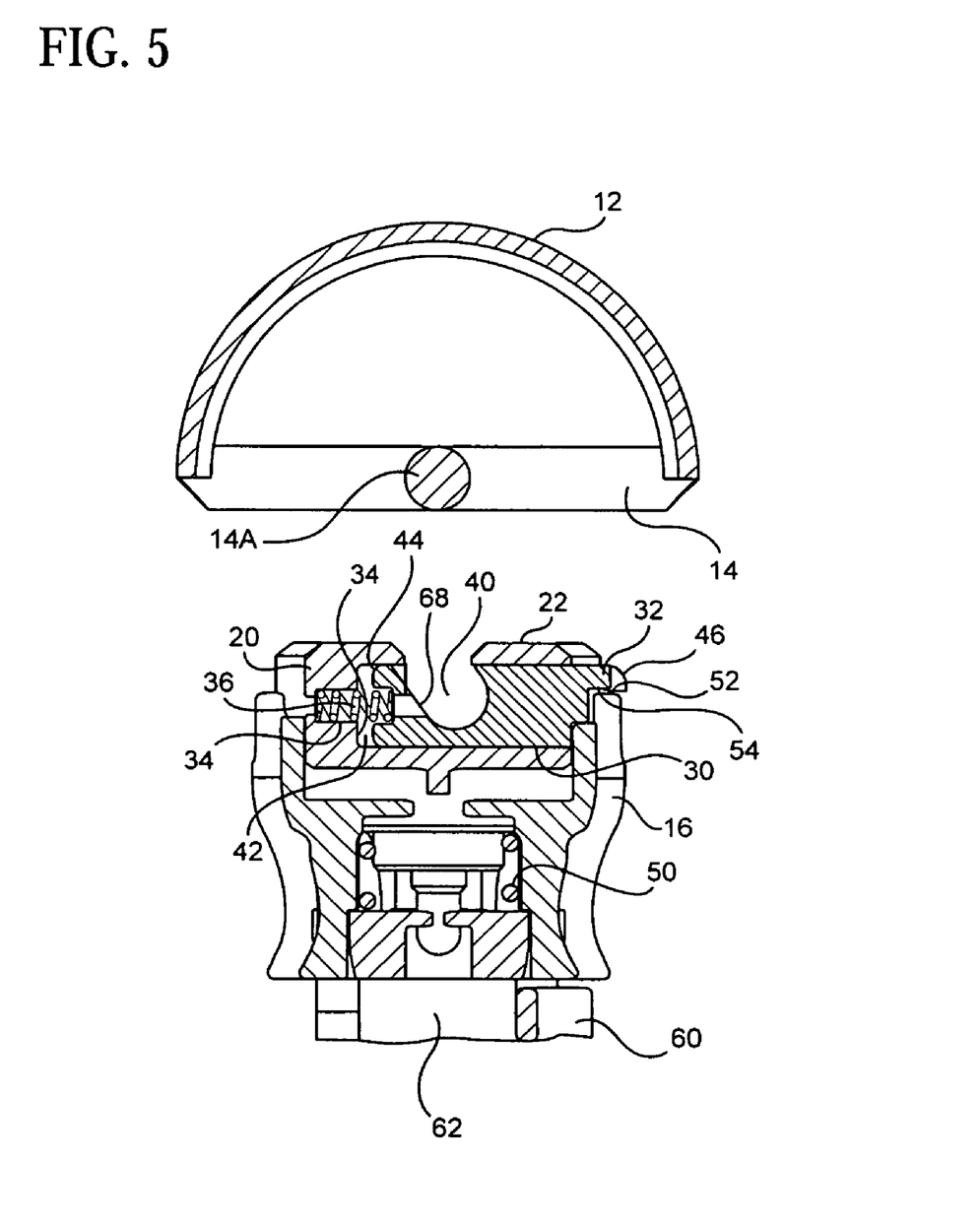
FIG. 5 is a cross sectional exploded view of the tool holder along lines 5-5 of FIG. 3 with the acetabular cup separated from the head portion of the tool holder, with the locking pin in a first position.

Referring to FIG. 4, there is shown a cross-sectional view of the tool mounting head 10 with acetabular reamer 12 mounted thereon via rods 14. Rods 14 are preferably mounted in grooves 18 of a body 20 of tool mounting head 11. Groove 18 is open to an upper surface 22 of head 20. Lock collar 16 is slidably mounted on the outer peripheral surface 24 of the lower portion 26 of mounting head body 20 and is spring biased towards reamer 12. Referring to FIG. 5 there is shown a second cross-sectional view of the mounting head/acetabular reamer combination shown in FIG. 3 with the reamer 12 separate from head 11. This view shows upper surface 22 of mounting head 20 and shows an internal bore 30 formed in body 20. Internal bore 30 houses a locking pin 32 which is biased away from a closed end 34 of bore 30 preferably by a coil spring 36. In the preferred embodiment coil spring 36 is mounted in a small counter bore 38 formed in body 20. Locking pin 32 includes a recessed area 40 which is adapted to receive a rod mounting element cross-section 14A when the locking element is in the first position shown in FIG. 5. This is the position where the coil spring 36 is expanded to form a gap 42 between end wall 34 of bore 32 and an end 44 of locking pin 32.

Locking pin 32 includes an extension 46 which extends outwardly of locking collar 16 when locking pin 32 is in the first position. Locking collar 16 is spring biased towards the upper surface 22 of body 20 by coil spring 50. Coil spring 50 biases locking collar 16 upwardly in FIG. 5 so that top surface 52 of locking collar 16 contacts stop surface 54 of locking pin 32 when locking pin 32 is in its first position. Also shown in FIG. 5 is non-rotatable handle 60 which includes a rotatable drive shaft 62 fixedly coupled to head 10. Consequently, tool mounting head 11 and locking collar 16 rotate with the drive shaft 62 about stationary handle 60. Obviously, when used with non-rotatable tools or implants, the quick head 10 could be non-rotatably mounted on the handle and the drive shaft eliminated.

Figure 6:
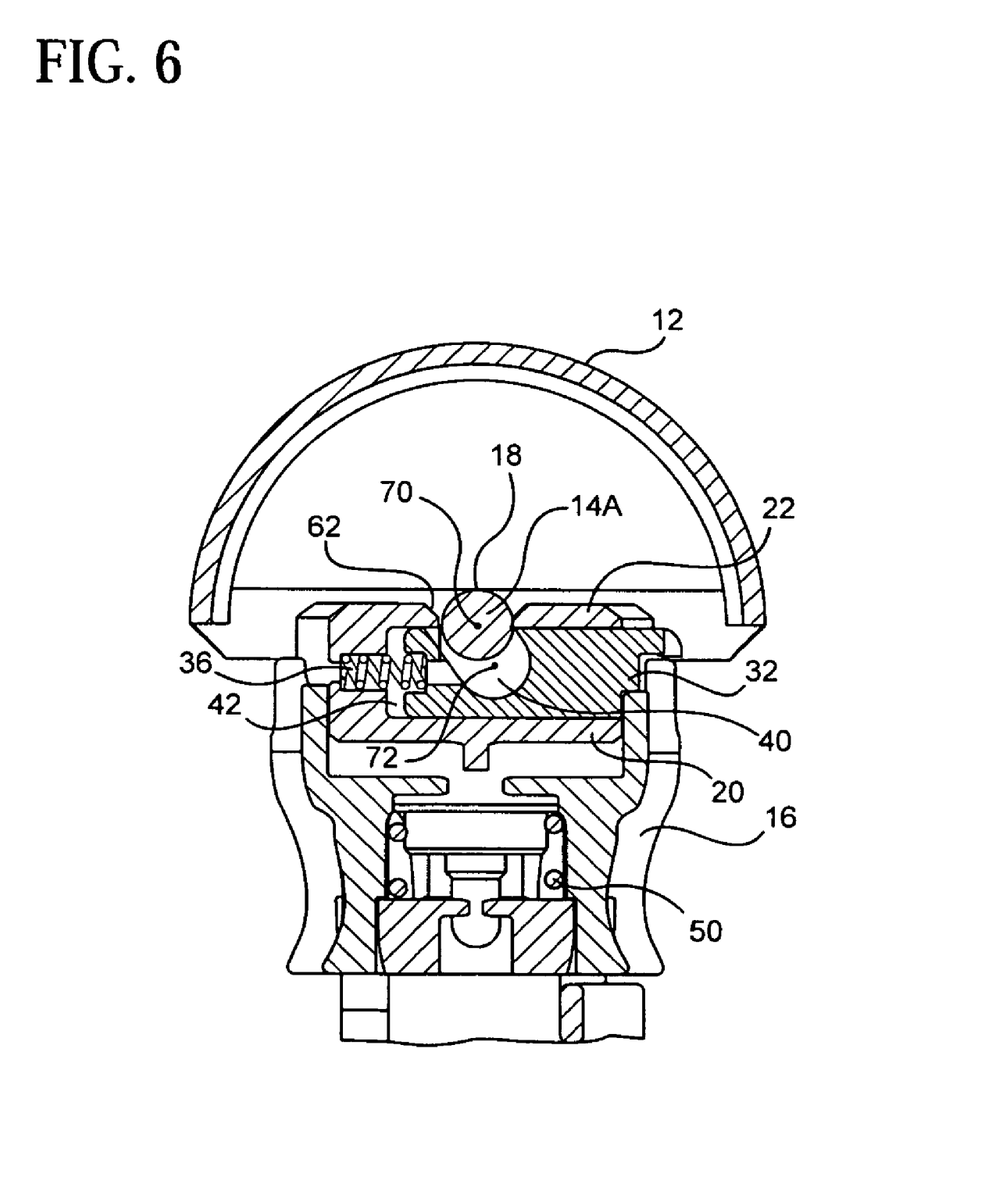
FIG. 6 is the cross section of FIG. 5 showing one of the mounting elements or rods at the position where it is initially introduced into the groove of the tool holder head and into a recess within the locking pin with the locking pin still in the fist position.
Figure 7:
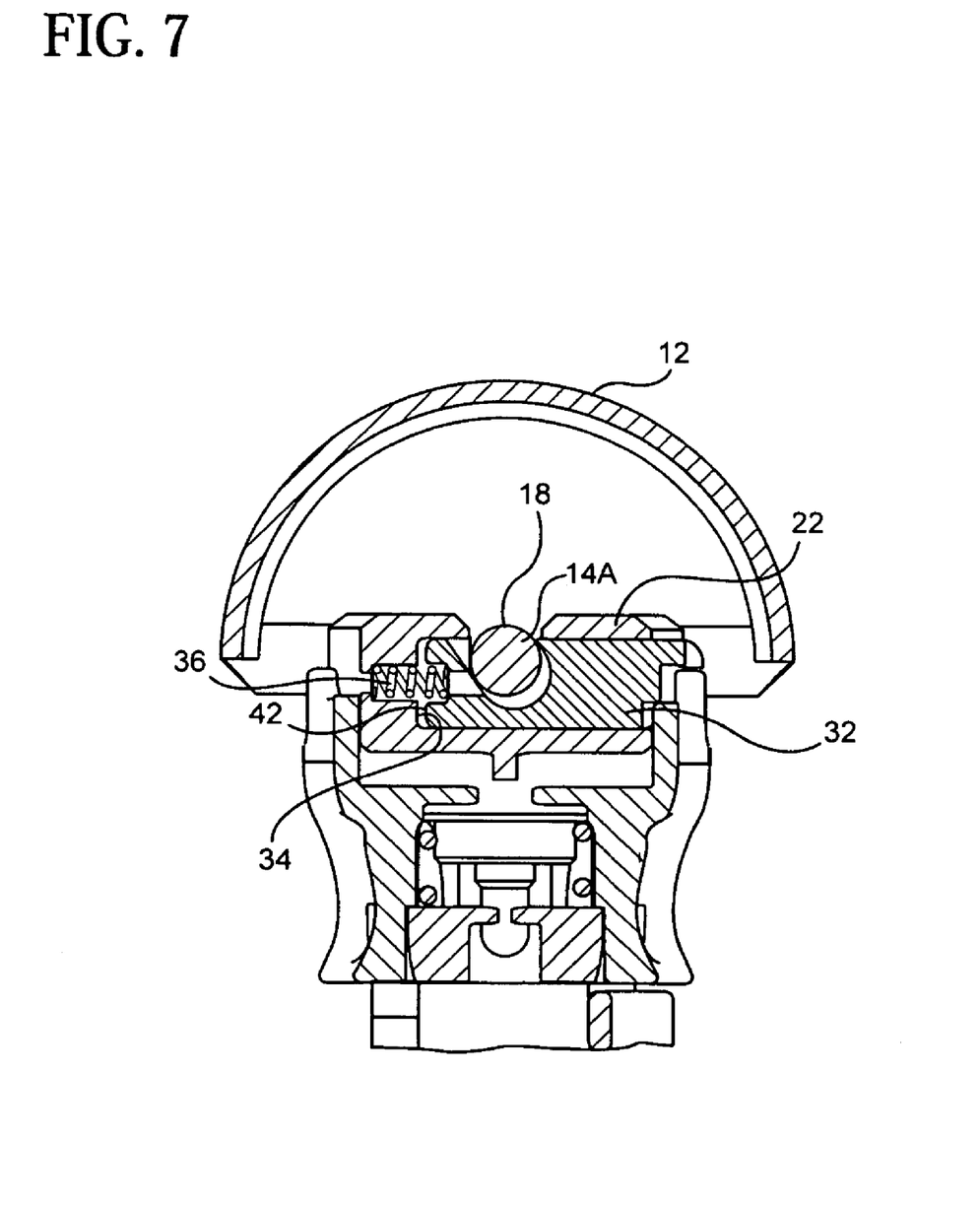
FIG. 7 is the cross-sectional view of FIG. 5 with the mounting element being inserted further into the recess of the locking pin thereby moving it towards a second position.
Figure 8:
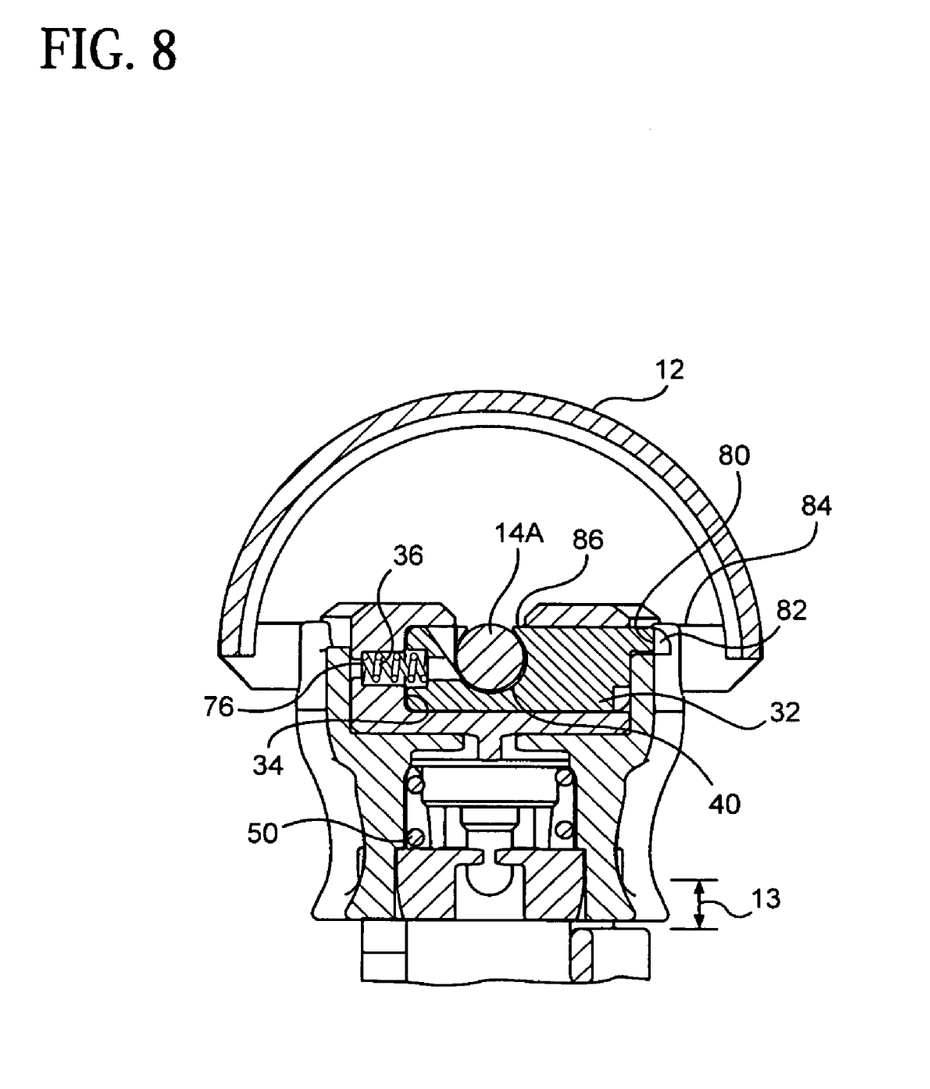
FIG. 8 is the cross-sectional view of FIG. 5 with the tool in the mounted position with the lock pin moved against the biasing spring into the second position.

Referring to FIGS. 6 through 8 there is shown a series of steps involved in coupling a tool to the tool mounting head 10 of the present invention. Initially, bar 14A is positioned at the entry of the open grooves 18 formed through face 22 of mounting head body 20. It should be noted that while the insertion of mounting element or rod section 14A will be described. It should be understood that in a cross-section on the opposite side of reamer 12 or if perpendicular lock pins were used in a groove perpendicular to that shown in FIG. 6 mounting element or rod 14 would be received in lock pin 32 in an identical manner.

With lock pin 32 in its first position, in which coil spring 36 biases lock pin 32 to form gap 42, the entrance of recess 40 is aligned with the walls 62 and 64 of groove 18. With the locking pin in this first position, locking collar 16 is biased upwardly in FIG. 5 by coil spring 50.

Referring to FIG. 7 there is shown mounting element 14A partially inserted into recess 40. Because the entrance of recess 40 is angled with respect to the long axis of locking pin 32 a cam surface 68 is formed. Consequently, at the initiation of insertion of rod 14A into recess 40 the center 70 of rod 14A is offset from the center 72 of a rod receiving base portion of recess 40. Thus, as rod 14A is moved downwardly within recess 40, the engagement of the outer diameter surface of rod 14A and cam surface 68 causes movement of locking pin 32 towards end wall 34 against the spring force of coil spring 36 thereby reducing gap 42. As best seen in FIG. 8, when rod 14A is at a second position fully seated within recess 40 of lock pin 32 end wall 76 of locking pin 32 engages end wall 34 of bore 30. In this second position of locking pin 32 top surface 52 of lock collar 16 disengages from stop surface 54 of locking pin 32 allowing lock collar 16 to move axially upward in the figures with a surface 80 adjacent end 32 of lock collar 16 engaging a surface 82 on lock pin 32 to prevent movement of lock pin 32 towards the first position. A ledge element 84 is formed on lock pin 32 and engages upper surface 52 of locking collar 16 to prevent any further upward axial movement thereof.

In this second position, a retaining portion 86 of lock pin 32 extends into groove 18, as best seen in FIG. 8 and prevents rod 14A from exiting recess 40. If it desired to remove the tool such as reamer 12 all the operator must do is pull downwardly on sleeve 16 against the biasing force of spring 50 which disengages surfaces 80 and 82 and allows pin 32 to move towards the first position under the force of spring 36. It should be noted that while in the preferred embodiment springs 36 and 50 are coil springs, any elastic element producing the required biasing forces could be utilized.

Figure 9:
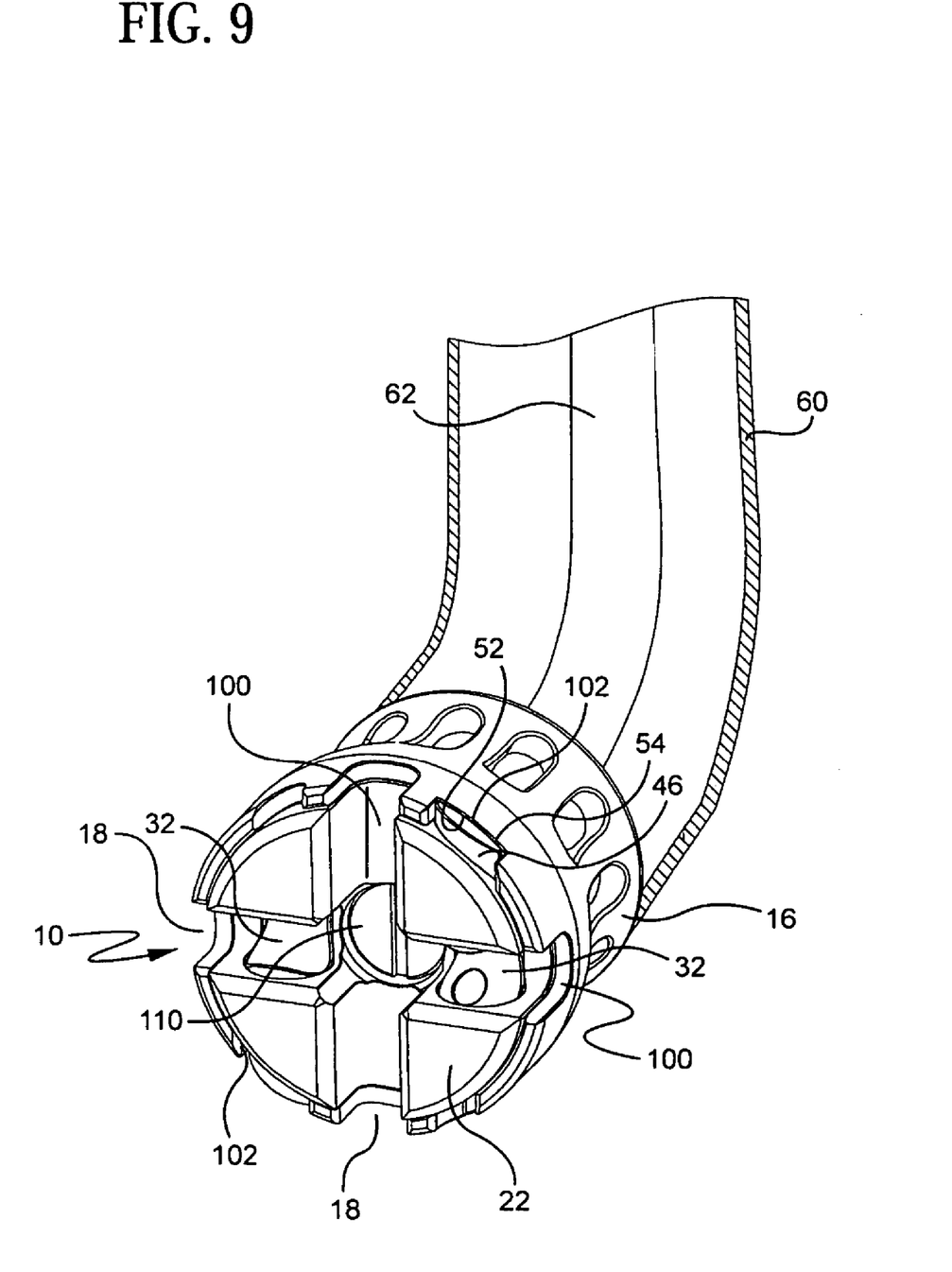
FIG. 9 is a perspective view of the tool mounting head of the present invention on a hollow handle which includes a rotary drive shaft to rotate the tool mounting head.

Referring to FIG. 9 there is shown a perspective view of the face 22 of tool mounting head 11. Also shown are grooves 18 and locking pins 32. Here it can be seen that lock collar 16 has, in the preferred embodiment, four recesses 100 for receiving rods 14, 14A and two recesses 102 having surface 52 which engages surface 54 of extending ledge 46 of locking pin 32. Also shown in FIG. 9 is hollow handle 60 and drive shaft 62. While handle 60 is shown as curved it could just as easily be straight and, as discussed above, if rotary motion is not required then rotary drive shaft 62 can be eliminated. In this situation, head assembly 10 would merely grip and release either a tool or an implant.

Figure 10:
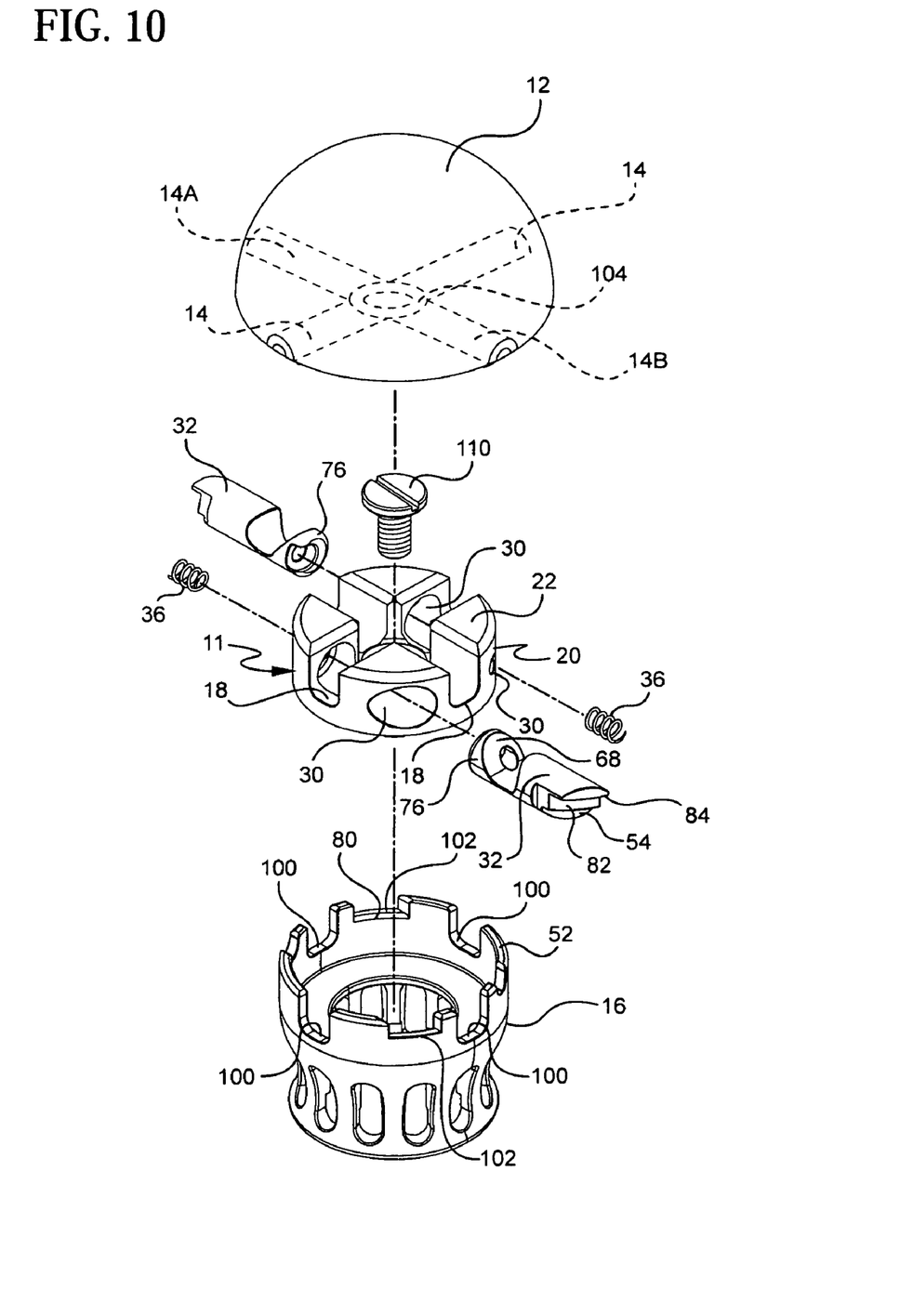
FIG. 10 is an exploded view of the tool mounting head of the present head of the present invention.
Figure 11:
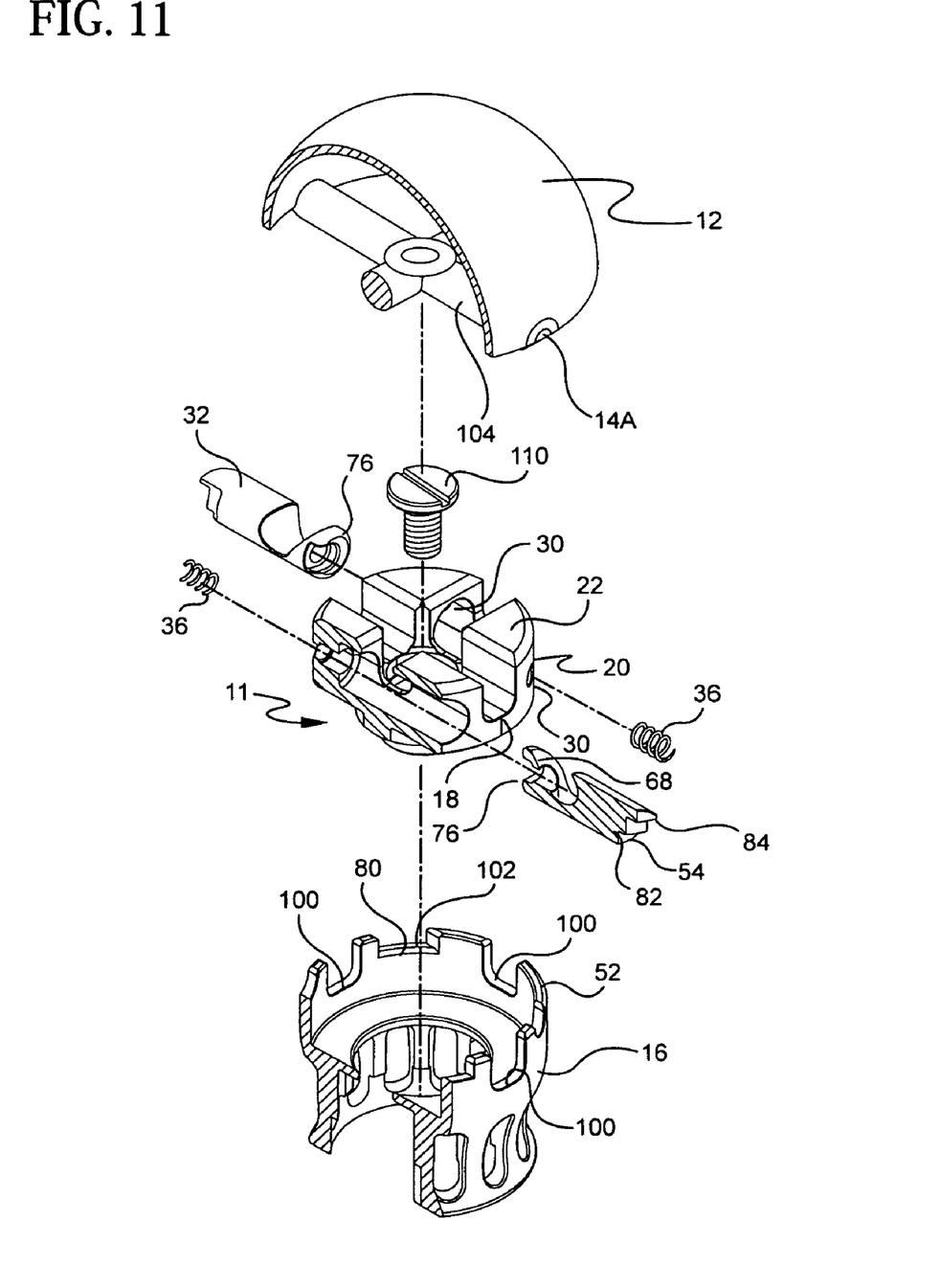
FIG. 11 is a partial perspective view of the tool holder shown in FIG. 10.

Referring to FIG. 10 there is shown a typical acetabular reamer 12 having four mounting elements in the form of rods 14 and 14A. In the preferred embodiment of the reamer 12 these rods extend from a central hub 104. As can be seen in both FIGS. 10 and 11 which are exploded views of the preferred mounting head 11 of the present invention which includes body 20. Body 20 includes an outwardly facing surface 22 with two radically extending grooves 18 open thereto. Body 20 also includes a pair of bores 30 in which locking pins 32 are mounted. Coil springs 36 are mounted in end 76 of lock pin 32. Also shown is screw 110 which is used to attach body 20 to the drive shaft 62. The four recesses 100, as well as the two recesses 102, are shown on locking collar 16. In addition, upper surface 52 of sleeve 16 is shown which engages stop surface 54 on locking pin 32 as well as contact surface 82 and outwardly extending ledge 84. Surface 82 engages surface 80 immediately below recess 102 when the locking pin is in the second position thereby preventing the locking pin 32 from moving within bore 30. When the locking pin is in the second position ledge 84 overlies surface 102 of locking collar 16 to prevent axial movement of lock collar 16.

Figure 12:
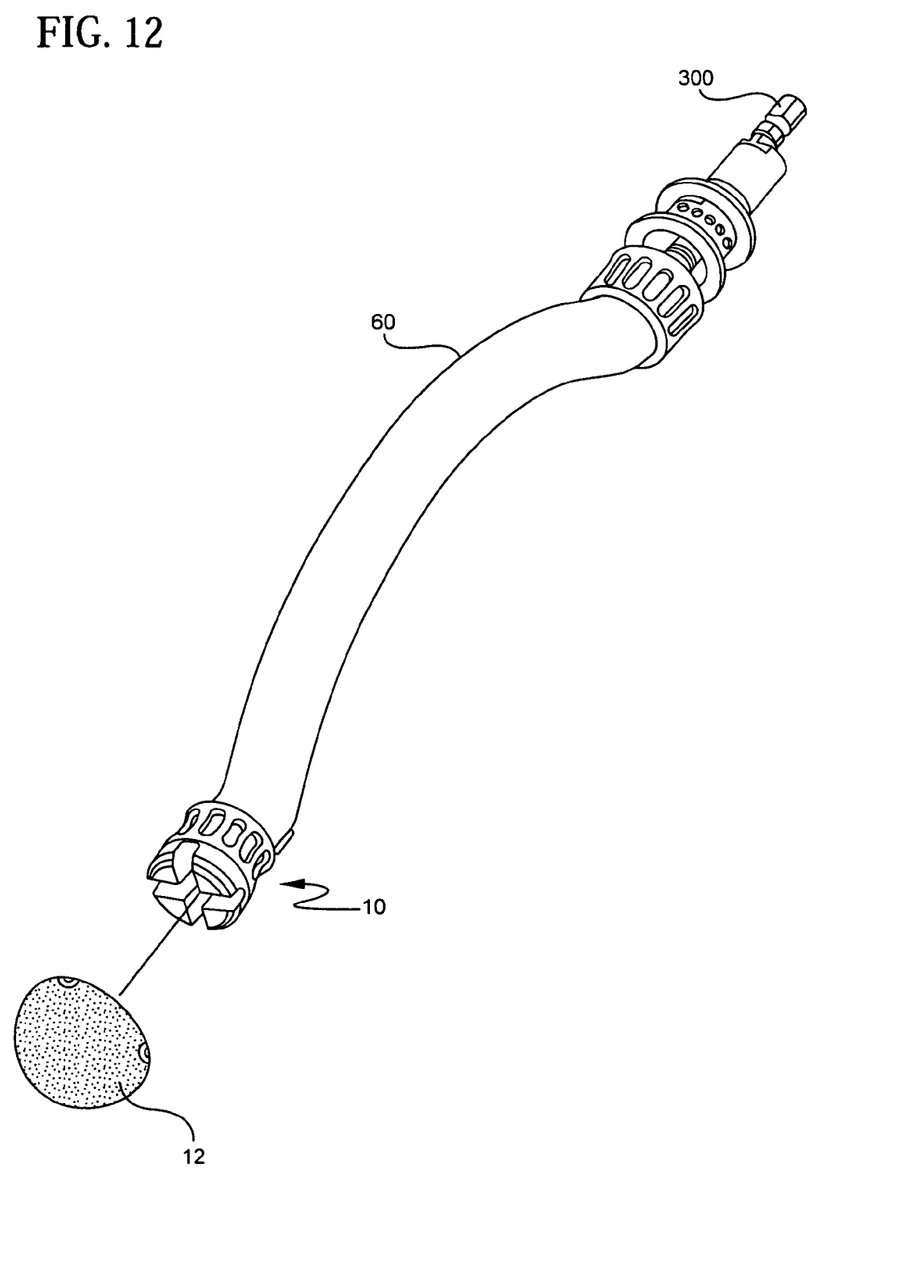
FIG. 12 is an isometric view of the tool holder of the present invention coupled to a curved handle having a power input end.

Referring to FIG. 12, there is shown the tool holder 10 mounted on a curved handle 60. Curved handle 60 is hollow and includes curve drive shaft 62 shown in FIG. 9. Also shown in FIG. 12 is a hex drive 300 which can be connected to any standard power source such as an electric or pneumatic drill.

To operate the quick connect/disconnect head assembly 10 the mounting bars 14, 14A of the tool are inserted in grooves 18 of body 20 and downward pressure is exerted against cam surface 68 causing locking pin 32 to compress springs 36. As mounting elements or rods 14, 14A move within recess 40 surfaces 52 and 54 disengage allowing sleeve 16 to move axially upwardly against the spring force of spring 50 and thus allow surface 80 to engage surface 82 closing gap 52 and causing the engagement of locking portion 86 of pin 32 to overlie rod 14A. When removal of the tool 12 is desired, the user grips sleeve 16 and moves it downwardly against the force of spring 50 which disengages surface 82 from surface 80 of sleeve 16 and allows the locking pin surface 54 to slide over surface 52 of sleeve 16 thereby moving portion 86 out of engagement with rods 14, 14A to allow the removal of the tool 12.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tool holder for releasably coupling a tool having a plurality of mounting elements to a drive shaft extending along an axis, the holder comprising:
   a head portion coupled to an end of a drive shaft, said head portion having a body with at least one outwardly open groove extending thereacross for receiving the mounting elements on the tool and a plurality of bores extending through said body in a direction transverse to a drive shaft axis in communication with said groove;
   a biased lock pin slidably mounted in each of said bores of said head portion, each of said lock pins having a recess thereon for receiving the mounting elements, elastic elements biasing said lock pins into a first open position wherein said lock pin recess is aligned with the groove in said head portion for receiving the mounting elements, each lock pin having a surface thereon engagable with said mounting element for moving said lock pin against said elastic element into a second locking position wherein at least a part of said recess is not aligned with said groove to lock said mounting elements within said recesses, said lock pin having a first and second stop surface;
   an elastically-biased lock collar slidably mounted on said head for movement in the direction of the drive shaft axis, said lock collar having a stop surface thereon for engaging said first and second stop surfaces on each of said lock pins, said lock collar biased into a position wherein said stop surface thereon engages said stop surfaces on said lock pins and wherein said stop surface of the lock collar disengages from said first stop surface on the lock pins and engages the second stop surface thereon when said lock pins move to said second position.

2. The tool holder as set forth in claim 1 wherein the head portion has at least one groove having two bores associated therewith, each bore having a spring-biased lock pin slidably mounted therein.

3. The tool holder as set forth in claim 2 wherein the two bores are parallel to one another and the head has two grooves which are perpendicular to one another.

4. The tool holder as set forth in claim 3 wherein said tool has four radially extending mounting elements in the form of rods extending outwardly from a central hub portion with two of said rods engaging in each of the grooves.

5. The tool holder as set forth in claim 4 wherein said four rods extend outwardly at 90° increments around said hub.

6. The tool holder as set forth in claim 4 wherein the lock collar includes recesses for receiving said rods.

7. The tool holder as set forth in claim 1 wherein said lock collar and said drive shaft and said head portion are rotatably mounted with respect to a handle.

8. The tool holder as set forth in claim 1 wherein said lock pin recess has a first open portion for receiving said mounting element and a part-cylindrical portion for seating said mounting element, a center of said part-cylindrical seating portion being offset from a center of said recess open portion in a direction of a longitudinal axis of said bore in said body portion.

9. The tool holder as set forth in claim 8 wherein a wall extending between said first and second lock pin recess portions forms said a cam surface which engages said mounting elements upon their insertion into said grooves and moves said lock pin to said second position.

10. The tool holder as set forth in claim 9 wherein a line connecting the centers of said first and second recess portions extends at an angle with respect to the longitudinal axis of the lock pin bore.

11. The tool holder as set forth in claim 1 wherein said lock pin element and said lock collar spring are coil springs.

12. A reaming system for reaming the acetabulum comprising:
    a hollow handle;
    a drive shaft extending along an axis mounted within said hollow handle;
    a reamer coupling head mounted on said drive shaft at an end thereof, said reamer coupling head having a body with an outwardly open groove extending thereacross for receiving a radially extending mounting rod on an acetabular reamer and a bore extending through said body in communication with said groove;
    a spring biased lock pin slidably mounted in the bore of said reamer coupling head body for movement in a direction transverse to the axis, said lock pin having a recess thereon for receiving the mounting rod, a spring biasing said lock pin into a first open position wherein said lock pin recess is aligned with the groove in said reamer coupling head body, the lock pin recess having a surface thereon engagable with said mounting rod for moving said lock pin against said spring into a second locking position upon insertion of said rod in said outwardly open groove wherein at least a part of said recess is not aligned with said groove to lock said mounting rod within said recess and said lock pin having first and second stop surfaces;
    a spring biased locking collar mounted on said drive shaft surrounding said reamer coupling head and moveable with respect to said reamer coupling head in an axial direction of said shaft, said lock collar having a stop surface thereon for engaging said first and second stop surfaces on said lock pin, said lock collar spring-biased into a position where said stop surface thereon engages said first stop surface on said lock pin to hold said lock collar in a retracted position when said lock pin is in said first position and cause movement of said lock collar into an extended position when said locking surface thereon engages the locking pin second stop surface.

13. The reaming system as set forth in claim 12 wherein said lock collar has two positions engaging said lock pin to maintain said lock pin in said first or second positions.

14. The reaming system as set forth in claim 12 wherein the head portion has at least one groove having a pair of bores associated therewith, each bore having a spring-biased lock pin slidably mounted therein.

15. The reaming system as set forth in claim 14 wherein the two bores are parallel to one another and the two grooves are perpendicular to one another.

16. The reaming system as set forth in claim 15 wherein said tool has four radially extending mounting rods extending outwardly from a central hub portion with two of said rods engaging in each of the grooves.

17. The reaming system as set forth in claim 16 wherein said four rods extend outwardly at 90° increments around said hub.

18. The reaming system as set forth in claim 16 wherein the lock collar includes recesses for receiving said rods.

19. The reaming system as set forth in claim 12 wherein said lock collar and said reamer coupling head are rotatably mounted with respect to said handle.

20. The reaming system as set forth in claim 12 wherein said lock pin recess has a first open portion for receiving said mounting element and a part-cylindrical portion for seating said mounting rod, a center of said part-cylindrical seating portion being offset from a center of said recess open portion in a direction of a longitudinal axis of said bore in said body portion.

21. The reaming system as set forth in claim 20 wherein a wall extending between said first and second lock pin recess portions forms said cam surface which engages said rods upon their insertion into said grooves and moves said lock pin to said second position.

22. The reaming system as set forth in claim 21 wherein a line connecting the centers of said first and second recess portions extends at an angle with respect to the longitudinal axis of the lock pin bore.

23. A system for preparing the acetabulum with a cutting tool comprising:
    a drive shaft extending along an axis;
    a coupling head mounted on the drive shaft at an end thereof, the coupling head having a body with an outwardly open groove extending thereacross along a plane perpendicular to the axis for receiving a radially extending mounting rod on an acetabular cutting tool and a bore extending through the body in a direction transverse to the drive shaft axis in communication with the groove;
    a spring biased lock pin slidably mounted in the bore of the coupling head body, the lock pin having a recess thereon for receiving the mounting rod, a spring biasing the lock pin into a first position wherein said lock pin recess is aligned with the groove in said coupling head body, the lock pin recess having a surface thereon engagable with the mounting rod for moving the lock pin against the spring biasing into a second position upon insertion of the mounting rod in the outwardly open groove wherein at least a part of the recess is not aligned with said groove to lock said mounting rod within the recess and the lock pin having first and second axially spaced stop surfaces;
    a spring biased locking collar mounted on said drive shaft surrounding said head and moveable with respect to said coupling head in the axial direction of the drive shaft, the lock collar having a surface thereon for engaging the first and second stop surface on the lock pin, the lock collar spring-biased along the shaft axis into a position where a surface thereon engages a stop surface on the lock pin to hold the locking pin in the second position and the locking collar is moved against the spring bias along the shaft axis to allow the locking pin to move to the first position and wherein the locking collar surface disengages from the first lock pin stop surfaces and engages the second lock pin stop surface when the lock pin moves to the second position.

* * * * *

UNITED STATES PATENT AND TRADEMARK OFFICE
CERTIFICATE OF CORRECTION

PATENT NO. : 7,513,899 B2 Page 1 of 1
APPLICATION NO. : 11/342206
DATED : April 7, 2009
INVENTOR(S) : Gregory Andrew Grim It is certified that error appears in the above-identified patent and that said Letters Patent is hereby corrected as shown below:

On the Title Page, Item (57), Abstract: line 15, after "pin" insert -- , --.
In Column 2, line 12, after second occurrence "spring", insert -- , --.
In Column 2, line 12, after "however" insert -- , --.
In Column 2, line 62, replace "being" with -- is --.
In Column 3, line 4, after "bore" insert -- , --.
In Column 3, line 24, replace "fist" with -- first --.
In Column 7, line 6, after "forms" delete "said".
In Column 8, line 53, replace "surface" with -- surfaces --.

Signed and Sealed this

Fourth Day of May, 2010

David J. Kappos
*Director of the United States Patent and Trademark Office*